United States Patent [19]

Kirchgeorg et al.

[11] Patent Number: 4,940,049

[45] Date of Patent: * Jul. 10, 1990

[54] GAS DISPENSING APPARATUS AND CASE THEREFOR

[75] Inventors: John Kirchgeorg, 1919 N. Summit Ave., Milwaukee, Wis. 53202; Michael G. Hermann, West Bend, Wis.

[73] Assignee: John Kirchgeorg, Milwaukee, Wis.

[*] Notice: The portion of the term of this patent subsequent to Dec. 6, 2005 has been disclaimed.

[21] Appl. No.: 425,501

[22] Filed: Oct. 23, 1989

Related U.S. Application Data

[60] Continuation of Ser. No. 206,448, Jun. 14, 1988, abandoned, which is a division of Ser. No. 862,685, May 13, 1986, Pat. No. 4,788,973.

[51] Int. Cl.$^5$ .................... A62B 7/02; A62B 9/04; A62B 25/00; A62B 37/00
[52] U.S. Cl. .................... 128/205.24; 128/205.25; 128/204.18
[58] Field of Search ............. 128/204.17, 204.18, 128/204.26, 203.17, 203.27, 202.27, 205.11, 205.25, 200.24, 205.24; 222/156, 154, 3; 312/138 R

[56] References Cited

U.S. PATENT DOCUMENTS

| 1,361,451 | 12/1920 | Flannery, Jr. | 312/138 R |
| 1,827,574 | 10/1931 | Frazier | 222/154 |
| 2,198,811 | 4/1940 | Gabriel | 222/156 |
| 2,552,783 | 5/1951 | Harper | 222/3 |
| 3,027,211 | 3/1962 | Wright | 312/138 R |
| 4,196,725 | 4/1980 | Gunderson | 128/205.25 |
| 4,618,067 | 10/1986 | Cohn et al. | 312/138 R |
| 4,621,633 | 11/1986 | Bowles et al. | 128/204.17 |
| 4,722,333 | 2/1988 | Bartos | 128/204.18 |

OTHER PUBLICATIONS

Hudson Oxygen Therapy Sales Co., Jun. 1, 1972, Hudson Lifesaving Equip., Elder Oxygen Company, Inc. ("Elder Demand Valve Resuscitation").

Primary Examiner—Clifford D. Crowder
Assistant Examiner—Kimberly L. Asher
Attorney, Agent, or Firm—Sughrue, Mion, Zinn, Macpeak & Seas

[57] ABSTRACT

A gas dispensing system particularly adapted for use as an emergency oxygen inhalator includes a gas storage tank and gas distributing apparatus enclosed in a case having an access opening therein. The access opening is opened and closed by means of a transparent cover which shows the tank and dispensing apparatus inside the case and makes it easy for a user to quickly find and use the oxygen inhalator.

17 Claims, 2 Drawing Sheets

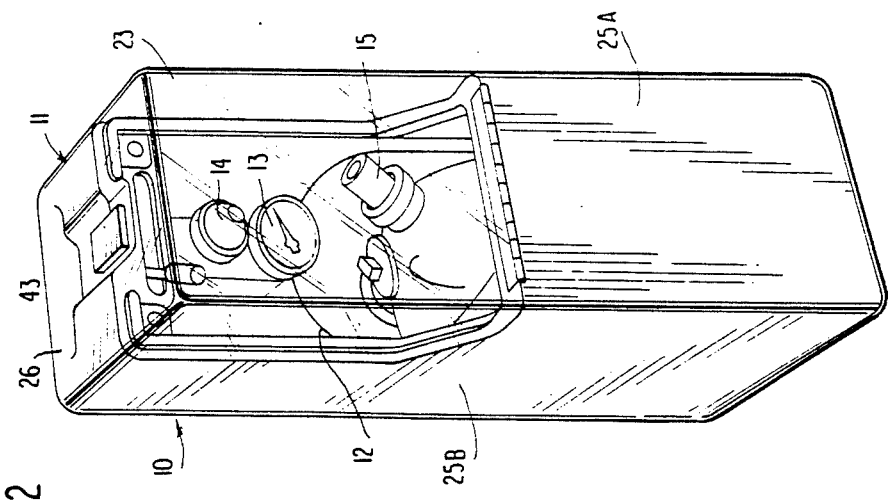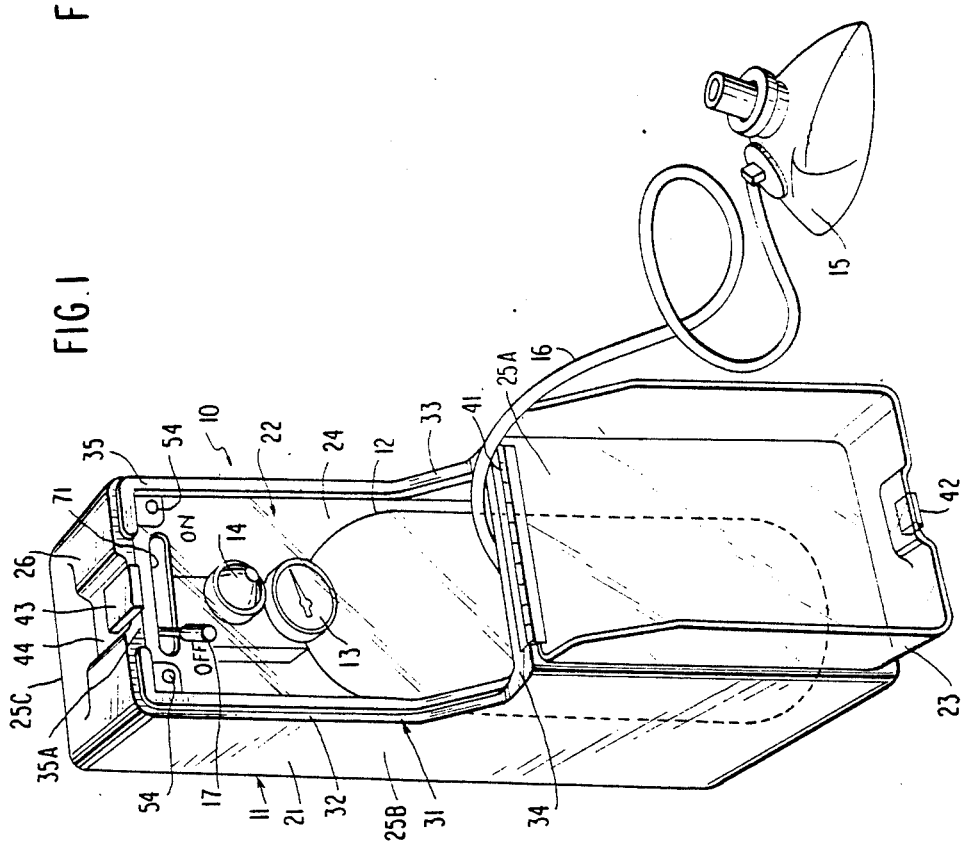

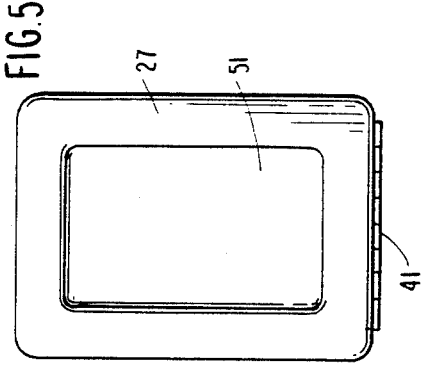
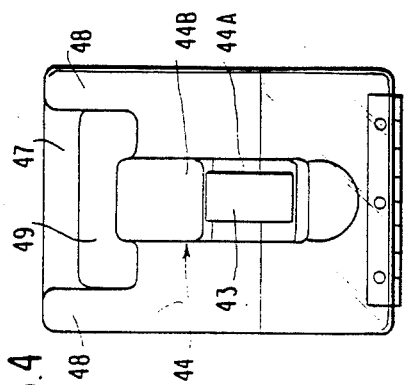
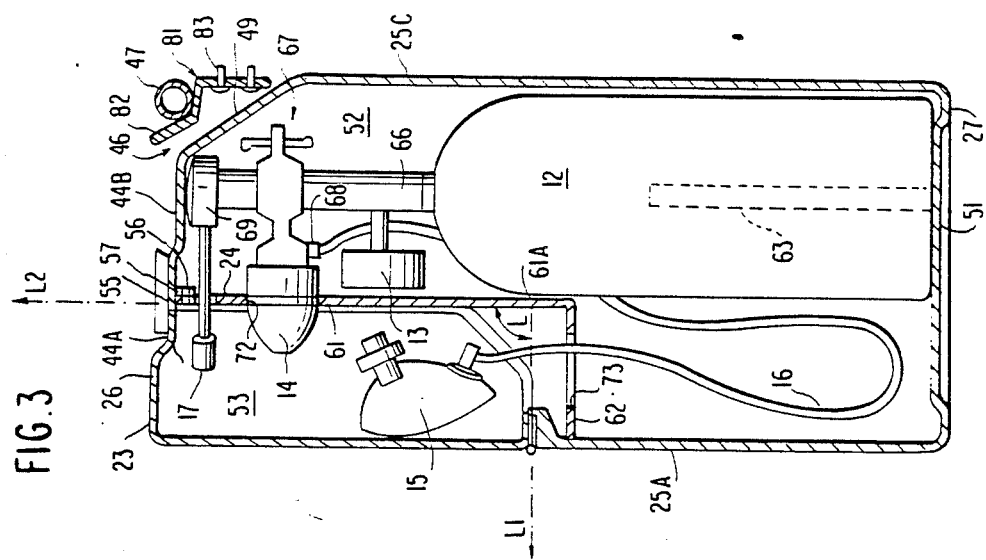

GAS DISPENSING APPARATUS AND CASE THEREFOR

This application is a continuation of Ser. No. 07/206,448, filed 6/14/1988, abandoned; which was a divisional of Ser. No. 06/862,685, filed 5/13/1986, now U.S. Pat. No. 4,788,973.

FIELD OF THE INVENTION

This invention pertains to a gas dispensing device including a case specially designed for ease of use and access. The case of this invention is particularly adapted for housing an emergency oxygen dispensing system.

BACKGROUND OF THE INVENTION

Known emergency oxygen dispensing units typically comprise a case containing a tank of oxygen and an oxygen mask connected to the tank by a flexible tube whereby the oxygen can be administered directly to a human patient. The following U.S. Patents illustrate oxygen dispensing devices, cases for containing or carrying such devices, and similar equipment: Eppolito U.S. Pat. No. 4,438,764 issued Mar. 27, 1984, Eppolito U.S. Pat. No. 4,383,528 issued May 17, 1983, Ansite U.S. Pat. No. 4,506,667 issued Mar. 26, 1985, Henneman et al. U.S. Pat. No. 4,186,735 issued Feb. 5, 1980, Warncke U.S. Pat. No. 3,277,890 issued Oct. 11, 1966, Almasi U.S. Pat. No. 4,359,048 issued Nov. 16, 1982, Bartlett, Jr. U.S. Pat. No. 3,208,449 issued Sept. 28, 1965, Oetjen U.S. Pat. No. 4,019,507 issued Apr. 26, 1977, Hauff U.S. Pat. No. 4,233,972 issued Nov. 18, 1980, Jarisabka U.S. Pat. No. 4,202,330 issued May 13, 1980, Beebe U.S. Pat. No. 4,560,193 issued Dec. 24, 1985, Fitt et al. U.S. Pat. No. 3,179,119 issued Apr. 20, 1965, McDonough U.S. Pat. No. 3,292,617 issued Dec. 20, 1966, van Amerongen et al. U.S. Pat. No. 3,804,280 issued Apr. 16, 1974, Warncke U.S. Pat. No. 3,483,887 issued Dec. 16, 1969, Cowley U.S. Pat. No. 3,505,997 issued Apr. 14, 1970, Haas U.S. Pat. No. 3,616,436 issued Oct. 26, 1971, Dann U.S. Pat. No. 3,507,297 issued Apr. 21, 1970, and Vernon U.S. Pat. No. 3,615,250 issued Oct. 26, 1971. In particular, Stewart U.S. Pat. No. 4,109,828, issued Aug. 29, 1978, and Berndt U.S. Pat. No. 2,831,607 issued Apr. 22, 1958, disclose inhalation apparatus housed within a substantially rectangular case having an access opening with a hinged cover. Such designs are representative of emergency oxygen units presently being sold, which units include a case having a cover or door which opens to reveal the oxygen mask, a dial for reading the oxygen level of the oxygen tank inside the case, and an on-off switch for turning on the oxygen supply.

Cases for such emergency oxygen systems are typically bulky, clumsy to use and intimidating to a potential user. For example, the inhalator according to the foregoing patent to Stewart is housed in a heavy, steel reinforced box that looks like a trunk or musical instrument case from the outside. In an emergency, it is difficult to see that this device is in fact an oxygen inhalator and can be opened at one top corner thereof. When the user succeeds in opening the door of the case for the Stewart inhalation device, the case appears to contain only an oxygen mask connected to a rubber tube, an oxygen pressure gauge built into a opaque metal plate, and an on-off switch extending through a slot in the same metal plate. No oxygen tank can be seen, and a panicked user might look into the case and believe that the tank is missing. The gauge of this device also actuates only when the on-off switch is in the on position, giving the false impression that the tank is empty (zero pressure) when the on-off switch is in the off position.

Other commercial inhalator designs suffer similar defects. Some are designed identically to musical instrument cases and could easily be mistaken for such. Others have multiple hinged doors and are so complex that they resemble "magic boxes" used by magicians. Still other designs are in the form of loose fabric backpacks which may be difficult to access in the event of an emergency and do not simplify the use of the inhalation apparatus for the user.

The present invention attempts to remedy the defects in prior art inhalators (oxygen dispensers) and similar gas dispensing devices, particularly in the design of the case which houses the gas tank and inhalation apparatus.

SUMMARY OF THE INVENTION

This invention provides a gas dispensing system having a case which renders the gas dispensing apparatus easier to use. The case according to the invention comprises housing having an access opening therein. The access opening is cut away from one end wall (the top wall) of the case and at least one side wall thereof. A transparent cover fits over the access opening.

The gas dispensing system according to the invention includes a gas dispensing apparatus, such as an oxygen inhalator, and a case according to the invention so that the oxygen mask, indicator dial, on-off switch, and gas tank (oxygen tank) are visible through the transparent cover. This dispels all doubt as to the manner of opening the case and makes it easy for a person to both identify and use the unit.

BRIEF DESCRIPTION OF THE DRAWING

A preferred exemplary embodiment of the invention is hereafter described in conjunction with the appended drawing, where in like numerals denote like elements, and:

FIG. 1 is a perspective view of a gas dispensing system according to the invention, in an unpacked state with the cover open;

FIG. 2 represents the same view as FIG. 1, with the gas dispensing apparatus packed inside and the cover closed;

FIG. 3 is a vertical sectional view of the gas dispensing system shown in FIG. 2 mounted on the wall rack shown in FIG. 7;

FIG. 4 is a top view of the gas dispensing system shown in FIG. 2;

FIG. 5 is a bottom view of the gas dispensing system shown in FIG. 2; and

FIG. 6 is a top view of the gas dispensing system shown in the FIG. 1, with the tube and mask removed, and showing the case in partial horizontal cross-section; and FIG. 7 is a front view of a wall rack for use with the invention.

DETAILED DESCRIPTION OF A PREFERRED EXEMPLARY EMBODIMENT

FIG. 1 illustrates a gas dispensing system 10 and a case 11 therefor particularly adapted for use as an emergency oxygen dispensing unit. Such an oxygen dispensing unit 10 includes a tank of pressurized oxygen 12, a pressure gauge 13 for indicating the supply of oxygen within tank 12, a regulator 14 for controlling flow of pressurized oxygen, an oxygen mask 15 having a flexible tube 16 connected thereto for conducting oxygen to the user, and an on-off switch 17 for starting and stopping the flow of oxygen through tube 16 to oxygen mask 15. Case 11 includes a substantially rectangular housing 21 having an access opening 22 therein, which access opening can be opened and closed by a transparent plastic cover 23. Case 11, further includes a transparent partition 24 which subdivides the interior of case 11, as will be described in detail below.

FIGS. 1 and 2 illustrate the structure of an exemplary case 11 according to the invention. Housing 21 of case 11 comprises at least one side wall 25 and a pair of top and bottom walls 26 and 27, respectively. Housing 21 is generally made of opaque, rigid plastic and is preferably one-piece, having only one opening (access opening 22) therein. In the embodiment shown, housing 21 is substantially rectangular, and has a front wall 25A, a pair of identical side walls 25B, 25D, and a rear wall 25C. Access opening 22 is defined by cutaway portions of top wall 26, front wall 25A, and side walls 25B, 25D. Access opening 22 opens to the front of unit 10.

Access opening 22 is generally large enough to define an included angle L in the lengthwise direction of case 11 of at least about ninety degrees. Angle L is usually 90 degrees when housing 21 is substantially rectangular, i.e. top wall 26 is substantially perpendicular to each of walls 25A–25D. In the illustrated embodiment, angle L is the angle between imaginary lines L1 and L2 shown in FIG. 3. Access opening 22 also defines an included angle W of at least 180 degrees in a direction (imaginary plane) perpendicular to the lengthwise direction of case 11, as illustrated in FIG. 6.

Housing 21 preferably comprises a quarter-open box, that is, a hollow rectangular casing having approximately a quarter thereof removed, as shown in FIG. 3. As indicated in FIGS. 1 through 3, access opening 22 extends the entire width and about half the length of front wall 25A, about one third the length and the entire width of top wall 26, and roughly half the length and one third the width of side walls 25B, 25D. Mouth 31 of access opening 22 includes an upper vertical portion 32, an intermediate outwardly sloping portion 33 which slopes downwardly from vertical portion 31, and a lower, horizontal portion 34. Horizontal and vertical directions referred to herein are relative to the orientation of Unit 10 as shown in the drawing. Mouth 31 has a shoulder (step) 35 on which transparent cover 23 rests when the unit is closed. Step 35 extends along the entirety of mouth 31, except for a top central portion 35A thereof. Upper vertical portion 32 of mouth 31 lies in an imaginary plane substantially parallel to the lengthwise axis of case 11. Sloping portion 33 similarly defines a imaginary plane with lies at an acute angle to the lengthwise axis of case 11, and horizontal lower portion 34 defines an imaginary plane which is perpendicular to the lengthwise axis of case 11.

Lower portion 34 of mouth 31 has a hinge 41 secured thereto whereby cover 23 is pivotally mounted to case 11. Hinge 41 adjoins shoulder 35 at horizontal mouth portion 34. Cover 23 and top wall 26 have a cooperating catch 42 and latch 43, respectively, for releasably securing cover 23 over access opening 22, as shown in FIG. 2.

Top wall 26 has a central split-level depression 44 in which latch 43 is situated. Latch 43 is mounted in the upper level 44A of depression 44, with lower level 44B behind latch 43 to facilitate ease of access to latch 43. Depression 44 allows tank 12 and the gas dispensing apparatus attached thereto to be removed from case 11 by tilting tank 12 forwardly and pulling it out of opening 22. In particular, the underside of lower level 44B snugly engages the top of a hub 69 of on-off switch 17, described further below. The underside of upper level 44A is sufficiently high to allow hub 69 to be tilted out through opening 22 for removing tank 12.

As shown in FIG. 4, top wall 26 can further include a cutaway portion 46 defining a handle 47 to facilitate carrying the unit. Handle 47 is round in cross-section and is conveniently disposed at a rear corner of housing 21 between a pair of symmetrical, rearwardly extending projections 48 formed at opposite sides of top wall 26. Opening 46 extends between handle 47 and a downwardly, rearwardly sloping rear portion 49 of top wall 26.

As illustrated in FIG. 5, bottom wall 27 is essentially flat, but may include an indentation 51 which forms a raised floor in the interior of case 11, on which tank 12 rests. Indentation 51 allows bottom wall 27 to sag to some extent under the weight of tank 12 without unduly deforming case 11 as a whole.

As shown in FIGS. 3 and 6, transparent partition 24 is substantially L-shaped in cross-section and partitions the interior of case 11 into an inner chamber 52 between transparent partition 24 and the inner surface of housing 21, and an essentially rectangular outer chamber 53 between transparent partition 24 and transparent cover 23. Transparent partition 24 is secured to a pair of tabs 56 which extend downwardly from top wall 26 near opposite upper corners of access opening 22 by fasteners (screws) 54 which extend through holes 55 in upper corners of transparent partition 24 and corresponding holes 57 in tabs 56.

Transparent partition 24 retains the oxygen dispensing apparatus, as illustrated in FIG. 3. Oxygen tank 12 rests on the inside surface of indentation 51 of bottom wall 27 at the bottom rear corner of inner chamber 52. Transparent partition 24 comprises a transparent vertical wall 61 and a transparent horizontal wall 62. A lower portion 61A of transparent vertical wall 61 abuts directly against tank 12 and secures tank 12 against the inside surface of rear wall 25C. This eliminates the need for additional means for securing tank 12 within housing 21, although a pair of opposing foam cushions 63 may be disposed on the inside surfaces of walls 25B, 25D where necessary to securely position tank 12 and prevent hose 16 from becoming caught or pinched between tank 12 and the inside of housing 21. Tank 12 is removable from housing 21 through access opening 22 upon removal of transparent cover 23 and transparent partition 24.

Tank 12 has a valve post 66 which is functionally connected to pressure indicator (gauge) 13 which extends from one side of valve post 66 and a gas dispensing assembly 67 connected to the top of valve post 66. Assembly 67 includes regulator 14, oxygen outlet 68 connected to one end of flexible tube 16, hub 69 and on-off switch 17, which projects forwardly from hub 69. Back and forth movement of switch 17 starts and stops the flow of air from outlet 68. Regulator 14 is screw-clamped over a valve outlet in valve post 66, receives oxygen from tank 12 when the valve is open, and regulates the level of flow thereof out of outlet 68. Pressure regulating valve assemblies of this general type are known, as illustrated in the above-cited patents to Stewart and Berndt, the contents of which are hereby incorporated by reference herein.

Oxygen dispensing apparatus according to the invention includes the above-described tank 12, gas dispensing assembly 67, hose 16 and mask 15. Transparent partition 24 conveniently separates the elements of the oxygen dispensing apparatus which the user needs access to from those elements of the apparatus which the user does not require access to. Specifically, on-off switch 17, which is a rod, extends through an elongated slot 71 near the upper end of transparent vertical wall 61 of transparent partition 24. Elongated slot 71 is typically centrally positioned directly between holes 55. Transparent vertical wall 61 further has a round hole 72 extending therethrough, which hole 72 is directly below elongated slot 71. Hole 72 is just large enough to allow part of regulator 14 to extend therethrough into outer chamber 53. This prevents tank 12 from turning inside case 11, and allows housing 21 to be made smaller overall. Pressure gauge 13, disposed directly below regulator 14 in the embodiment shown, is directly behind vertical wall 61 of transparent partition 24 and is visible through both of transparent portion 24 and transparent cover 23.

Horizontal wall 62 of transparent partition 24 has a hole 73 extending therethrough. Flexible tube 16 extends from oxygen outlet 68 within inner chamber 52 through hole 73 to oxygen mask 15 disposed in outer chamber 53. In this manner excess length of tube 16 can be stored in the front portion of inner chamber 52, drawn out as needed to use the unit, as illustrated in FIG. 1, and then returned to inner chamber 52 by reinserting tube 16 into hole 73. Hole 73 is sufficiently large to readily admit tube 16 without jamming or catching, but is sufficiently small to prevent oxygen mask 15 from falling downwardly into inner chamber 52.

As illustrated in FIGS. 3 and 7, unit 10 can be wall mounted on a wall rack 81 by lifting handle 47 over and onto upwardly, outwardly extending portion 82 of rack 81. Rack 81 is mounted to a wall by any suitable means, such as screws 83 inserted through holes 84. Rack 81 preferably comprises a first end wall 86, a second intermediate wall 87 which is substantially perpendicular to wall 86, and a second end wall 88 which extends at an obtuse angle relative to intermediate wall 87. Since handle 47 is positioned at an upper corner of case 11, it can serve both for carrying the unit 10 and for hanging unit 10 on rack 81. This advantage is not provided by conventional handles centrally mounted on one wall of a case or housing.

Operation of oxygen dispensing unit 10 according to the invention is as follows. With unit 10 in the condition shown in FIG. 2, the user can immediately see what case 11 contains and which way it should be oriented for opening. The user lifts latch 43 to release it from catch 42, and then pivots transparent cover 23 around hinge 41 so that cover 23 assumes the position shown in FIG. 1. The user then grasps oxygen mask 15, positions it appropriately, and moves switch 17 to the on position, initiating the flow of oxygen through tube 16 to mask 15.

After oxygen inhalation is completed, the user returns switch 17 to the off position, replaces tube 16 and mask 15 into outer chamber 53 of the unit 10, and then closes cover 23 by pivoting it upwardly and engaging latch 43 with catch 42. Unit 10 thereby resumes the configuration shown in FIG. 2. The user should not normally need to remove transparent partition 24 to access the parts of the unit disposed in inner chamber 52. This helps assure that the essential working parts of the unit, such as gas dispensing assembly 67, will not be tampered with.

It will be understood that the above description is of a preferred exemplary embodiment of the invention, and that the invention is not limited to the specific forms shown. For example, housing 21 could be made cyclindrical and have a single wall 25. Tank 12 can contain a pressurized gas other than oxygen, to be used for any desired purpose. These and other modifications may be made in the design and arrangement of the elements without departing from the scope of the invention as expressed in the appended claims.

We claim:

1. An oxygen delivery system, comprising:
   a unitary one piece housing including an end wall, and at least two side walls including a front wall, said housing having an access opening in at least said front wall;
   oxygen delivery means enclosed within said housing, said oxygen delivery means including at least an oxygen bottle, valve means connected to said oxygen bottle for regulating the flow of oxygen from said bottle, oxygen conducting means connected to said valve means, and a mask connected to said oxygen conducting means;
   said access opening being shaped and sized such as to permit insertion and removal of said oxygen bottle and said valve means into and out of said housing;
   a transparent cover positionable over said access opening, said mask and said oxygen bottle being positioned within said housing such that substantially all of said mask and at least an upper portion of said oxygen bottle are clearly visible from the exterior of said housing when said transparent cover is closed.

2. The delivery system of claim 1, wherein said housing is substantially rectangular and has a fixed top wall, four side walls including said front wall, said access opening being formed in said fixed top wall, said front wall and two others of said side walls.

3. The delivery system of claim 2, wherein said housing further comprises a depression located at said top wall, said oxygen bottle and said valve means together being snugly engaged between said depression and said end wall when said oxygen bottle and said valve means are positioned within said housing, to restrict vertical movement of said oxygen bottle and said valve means within said housing.

4. The delivery system of claim 1, wherein said housing is substantially rectangular and has a fixed top wall, two side walls, a rear wall and said front wall, said access opening being formed in said fixed top wall and said front wall.

5. The delivery system of claim 4, wherein said housing further comprises a depression located at said fixed top wall, said oxygen bottle and said valve means together being snugly engaged between said depression and said end wall when said oxygen bottle and said valve means are positioned within said housing, to restrict vertical movement of said oxygen bottle and said valve means within said housing.

6. An oxygen delivery system as claimed in claim 1, wherein said housing is substantially rectangular and includes a fixed top wall, said fixed top wall and said access opening being formed such that said removal of said oxygen bottle is accomplished by tilting said bottle toward said opening and then pulling said bottle through said opening.

7. An oxygen delivery system, comprising;
 (a) a unitary one-piece housing including a bottom wall, a fixed top wall, and front, back and side walls;
 (b) an access opening formed in at least said top wall and said front wall;
 (c) oxygen delivery apparatus disposed within said housing, including at least a tank and oxygen conducting means which terminates in a mask;
 (d) a transparent cover positionable over said access opening; and
 (e) said access opening being sized and said fixed top wall being designed so that said oxygen delivery apparatus may be removed from said unitary one-piece housing by tilting said tank toward said opening then pulling it out through said opening.

8. An oxygen delivery system as claimed in claim 7, wherein said fixed top wall includes a split-level depression therein, and wherein a lower level of said depression is located toward the back wall of said housing and normally engages a top surface of said oxygen delivery apparatus, and wherein an upper level of said depression located toward the front wall of said housing is set at a height sufficient to enable said tilting of said tank.

9. An oxygen delivery system as claimed in claim 8, wherein said split-level depression is formed as an integral part of said unitary one-piece housing.

10. An oxygen delivery system, comprising;
 (a) a unitary one-piece housing including a bottom wall, a fixed top wall, and front, back and side walls;
 (b) an access opening formed in said top wall, said front wall and said side walls, and comprising an approximate open quarter of said one-piece housing;
 (c) oxygen delivery apparatus disposed within said housing, including at least a tank and oxygen conducting means which terminates in a mask;
 (d) a transparent cover positionable over said access opening; and
 (e) said access opening being sized and said fixed top wall being designed so that said oxygen delivery apparatus may be removed from said unitary one-piece housing by tilting said tank toward said opening then pulling it out through said opening.

11. An oxygen delivery system, comprising;
 (a) a unitary one-piece housing including a bottom wall, a fixed top wall, and front, back and side walls;
 (b) an access opening formed in said top wall, said front wall and said side walls, and comprising an approximate open quarter of said one-piece housing;
 (c) oxygen delivery apparatus disposed within said housing, including at least a tank and oxygen conducting means which terminates in a mask;
 (d) a cover positionable over said access opening; and
 (e) said access opening being sized and said fixed top wall being designed so that said oxygen delivery apparatus may be removed from said unitary one-piece housing by tilting said tank toward said opening then pulling it out through said opening.

12. A gas dispensing system, comprising:
 an integral one-piece housing of rigid plastic having a pair of end walls comprising a fixed top wall and a bottom wall, and at least one side wall, said housing having a single access opening defined in one of said end walls and in a portion of at least said one side wall;
 a transparent cover removably disposed over said access opening;
 a partition secured to said housing for partitioning the interior of said housing into an inner chamber located between an interior surface of said housing and a rear surface of said partition, and an outer chamber located between a front surface of said partition and the interior of said cover;
 a tank disposed within said inner chamber; gas delivery means extending from said tank to said outer chamber and terminating in a mask, said outer chamber serving as a housing for said mask;
 said partition being substantially L-shaped and having a bottom surface positioned approximately at mid-section of said tank, and generally supporting said mask, the position of said bottom surface and the extent of said transparent cover being such that said mask is substantially fully visible through said transparent cover when said cover is closed;
 said access opening being shaped and sized and said fixed top wall being designed so that said oxygen delivery apparatus may be removed from said integral one-piece housing by tilting said tank toward said opening and then pulling it out through said opening.

13. A gas dispensing system, comprising:
 an integral one-piece housing of rigid plastic having a pair of end walls comprising a fixed top wall and a bottom wall, and at least one side wall, said housing having a single access opening defined in one of said end walls and in a portion of at least said one side wall;
 a transparent cover removably disposed over said access opening;
 a partition secured to said housing for partitioning the interior of said housing into an inner chamber located between an interior surface of said housing and a rear surface of said partition, and an outer chamber located between a front surface of said partition and the interior of said cover, said partition being substantially L-shaped and having a bottom surface which is substantially parallel to at least one end wall, said partition generally following the shape of said access opening but having a length which is greater than the length of said access opening such that said bottom surface sits in a plane below the lowermost extent of said access opening;
 a tank disposed within said inner chamber; gas delivery means extending from said tank to said outer chamber and terminating in a mask, said outer chamber serving as a housing for said mask;
 said partition generally supporting said mask, the position of said bottom surface and the extent of said transparent cover being such that said mask is substantially fully visible through said transparent cover when said cover is closed;
 said access opening being shaped and sized and said fixed top wall being designed so that said oxygen delivery apparatus may be removed from said integral one-piece housing by tilting said tank toward said opening and then pulling it out through said opening.

14. A gas dispensing system, comprising:

an integral one-piece housing of rigid plastic having a pair of end walls comprising a fixed top wall and a bottom wall, and at least one side wall, said housing having a single access opening defined in one of said end walls and in a portion of at least said one side wall;

a cover removably disposed over said access opening;

a partition secured to said housing for partitioning the interior of said housing into an inner chamber located between an interior surface of said housing and a rear surface of said partition, and an outer chamber located between a front surface of said partition and the interior of said cover, said partition being substantially L-shaped and having a bottom surface which is substantially parallel to at least one end wall, said partition generally following the shape of said access opening but having a length which is greater than the length of said access opening such that said bottom surface sits in a plane below the lowermost extent of said access opening;

a tank disposed within said inner chamber; gas delivery means extending from said tank to said outer chamber and terminating in a mask, said outer chamber serving as a housing for said mask;

said partition generally supporting said mask;

said access opening being shaped and sized and said fixed top wall being designed so that said oxygen delivery apparatus may be removed from said integral one-piece housing by tilting said tank toward said opening and then pulling it out through said opening.

15. An oxygen delivery system, comprising;
(a) a unitary one-piece housing including a bottom wall, a fixed top wall, and front, back and side walls;
(b) an access opening formed in said top wall, said front wall and said side walls, and comprising an approximate open quarter of said one-piece housing;
(c) oxygen delivery apparatus disposed within said housing, including at least a tank and oxygen conducting means which terminates in a mask;
(d) a cover positionable over said access opening;
(e) said access opening being sized and said fixed top wall being designed so that said oxygen delivery apparatus may be removed from said unitary one-piece housing by tilting said tank toward said opening then pulling it out through said opening;

(f) said housing including an internal depression located in said fixed top wall, said tank means and a portion of said oxygen conducting means being wedged between said fixed top wall at said depression and said bottom wall when said tank and said oxygen conducting means are positioned within said housing.

16. A gas dispensing system, comprising:
a housing having a pair of end walls comprising a fixed top wall and a bottom wall, and at least one side wall, said housing having an access opening in one of said end walls and in said one side wall;
a cover removably disposed over said access opening;
a partition secured to said housing for partitioning the interior of said housing into an inner chamber located between an interior surface of said housing and a rear surface of said partition, and an outer chamber located between a front surface of said partition and the interior of said cover;
a tank disposed within said inner chamber; gas delivery means extending from said tank to said outer chamber and terminating in said outer chamber, said outer chamber serving as a housing for a portion of said gas delivery means;
said partition being substantially L-shaped and having a bottom surface positioned approximately at a mid-section of said tank, and generally supporting said portion of said gas delivery means;
said access opening being shaped and sized and said fixed top wall being designed so that said oxygen delivery apparatus may be removed from said integral one-piece housing by tilting said tank toward said opening and then pulling it out through said opening.

17. An oxygen delivery system, comprising:
(a) a unitary one-piece housing including a bottom, a fixed top wall, and at least one peripheral wall;
(b) an access opening formed in said top wall and in at least a part of said peripheral wall, and comprising an approximate open quarter of said one-piece housing;
(c) oxygen delivery apparatus disposed within said housing, including at least a tank and oxygen conducting means which terminates in a mask;
(d) a cover positionable over said access opening; and
(e) said access opening being sized and said fixed top wall being designed so that said oxygen delivery apparatus may be removed from said unitary one-piece housing by tilting said tank toward said opening and then pulling it out through said opening.

* * * * *